United States Patent [19]
Subjeck

[11] Patent Number: 5,986,170
[45] Date of Patent: Nov. 16, 1999

[54] MURINE MODEL FOR HUMAN CARCINOMA

[75] Inventor: Elizabeth Repasky Subjeck, Williamsville, N.Y.

[73] Assignee: Corixa Corporation, Seattle, Wash.

[21] Appl. No.: 08/556,659

[22] Filed: Nov. 13, 1995

[51] Int. Cl.[6] .............................. C12N 5/00; C12N 5/10
[52] U.S. Cl. .............................. 800/2; 424/9.2; 435/325
[58] Field of Search .............................. 800/2; 424/9.2; 435/325

[56] References Cited

U.S. PATENT DOCUMENTS 5,399,346  3/1995  Anderson et al. ............... 424/93.21
5,569,812  10/1996  Monosov et al. .............. 800/2

FOREIGN PATENT DOCUMENTS

0322240A2  6/1989  European Pat. Off. .
0469632A1  2/1992  European Pat. Off. .
WO 91/16910  11/1991  WIPO .
WO 93/02687  2/1993  WIPO .

OTHER PUBLICATIONS

Xu, Y. et al., Coengrafment of Human Primary Breast Carcinoma & Autologous Immunocompetent Cells in SCID Mice. American Assoc. Cancer Research, Annual Meeting, Mar. 1995.

Sakakibara, T. et al., Engraftment and Growth of Patients' Breast Carcinoma in SCID Mice, San Antonio Breast Cancer Symposium, submitted Jun. 1994.

Bachmann et al. "In vivo versus in vitro assays for assessment of T—and B—cell Functionl," *Current Opinion in Immunology*, vol. 6 (2):320–326, 1995.

Outzen et al. "Growth of human normal and neoplastic mammary tissues in the cleared mammary fat pad of the nude mouse," *J. Nat. Cancer Inst.*, vol. 55(6): 1461–1466, 1975.

Bennett et al., "Accurate Prediction of Experimental Cancer Chemosensitivity Using the Subrenal Capsule Xenograft Assay," *Journal of Surgical Oncology* 33:8–13, 1986.

Bumpers et al., "Consistent Hepatic Metastasis of Human Colorectal Cancer in Severe Combined Immunodeficient Mice," *Journal of Surgical Research* 61:282–288, 1996.

Hagiwara et al., "Milky Spots as the Implantation Site for Malignant Cells in Peritoneal Dissemination in Mice," *Cancer Research* 53:687–692, 1993.

Niederberger et al., "Differences Between Subcutaneous and Intraperitoneal Forms of Three Human Testicular Teratocarcinomas in Nude Mice," *Cancer* 61:1571–1578, 1988.

Russell et al., "Bladder Cancer Xenografts: A Model of Tumor Cell Heterogeneity," *Cancer Research* 46(4):2035–2040, 1986.

Yano et al., "Inhibition of growth of MCF–7 MIII human breast carcinoma in nude mice by treatment with agonists or antagonists of LH–RH," *Breast Cancer Research and Treatment* 21:35–45, 1992.

*Primary Examiner*—Jasemine C. Chambers
*Assistant Examiner*—Karen M. Hauda
*Attorney, Agent, or Firm*—Seed and Berry LLP

[57] ABSTRACT

A murine model for human ovarian and prostate cancer is provided. The model comprises an immunodeficient mouse containing human primary ovarian or prostate carcinoma tissue implanted within the gonadal fat pad. Methods of using the murine model, for example, to grow tumors and to screen treatments for ovarian and/or prostate cancer are also provided.

15 Claims, No Drawings

5,986,170

MURINE MODEL FOR HUMAN CARCINOMA

TECHNICAL FIELD

The present invention relates generally to murine models for the growth of patients' breast, ovarian and prostate cancers. The invention is more particularly related to immunodeficient mice containing surgical specimens of human primary breast, ovarian or prostate carcinomas implanted within the gonadal fat pad. The present invention is also directed to methods for using such tumor-bearing mice, for example, to evaluate the effectiveness of treatments for breast, ovarian and/or prostate cancer or to identify carcinoma-associated antigens.

BACKGROUND OF THE INVENTION

Animal models for human carcinomas are valuable tools for the investigation and development of cancer therapies. However, several human carcinomas have proven exceptionally difficult to grow in animal models. For example, in spite of considerable effort, surgical specimens of human breast carcinomas have been resistant to growth in a variety of animal model systems, including the anterior chamber of the eye of guinea pigs, lethally irradiated or thymectomized mice and nude and SCID mice. In nude mice, the incidence of tumor take is low even when the animals are supplemented with estrogen, and those tumors that do grow exhibit amplification of the HER-2/neu oncogene, which has been correlated with poor prognosis. Thus, the best of the present models are only effective for a limited category of extremely malignant carcinomas, and no acceptable animal models are presently available for the general experimental study of human breast cancer. The need for animal models is even greater for human prostate and ovarian cancers where, to date, less research has been conducted.

Accordingly, there is a need in the art for improved animal models for the study of human breast, ovarian and prostate cancers. The present invention fulfills these needs and further provides other related advantages.

SUMMARY OF THE INVENTION

Briefly stated, the present invention provides murine models for breast, ovarian and prostate carcinomas. In one aspect, an immunodeficient mouse containing human primary breast, ovarian or prostate carcinoma tissue is provided, wherein the carcinoma tissue is implanted within a gonadal fat pad of the immunodeficient mouse.

Within related aspects, the present invention provides methods for generating a murine model for breast, ovarian or prostate cancer. In one embodiment, the method comprises implanting a specimen of a human breast, ovarian or prostate carcinoma within the gonadal fat pad of an immunodeficient mouse. In a related embodiment, the method further comprises removing a portion of the implanted carcinoma specimen and subsequently implanting the portion within a gonadal fat pad of a second immunodeficient mouse.

In yet another aspect, methods are provided for growing human breast, ovarian or prostate carcinoma tissue, comprising: (a) implanting a specimen of a human breast, ovarian or prostate carcinoma within a gonadal fat pad of an immunodeficient mouse; and (b) allowing the carcinoma to grow within the immunodeficient mouse.

In further aspects, the present invention provides methods for evaluating the effectiveness of a breast, ovarian or prostate cancer therapy, comprising: (a) implanting a specimen of a human breast, ovarian or prostate carcinoma within a gonadal fat pad of an immunodeficient mouse; (b) exposing the immunodeficient mouse to a candidate therapy; and (c) determining a change in size of the implanted specimen, the extent of tumor cell death and/or the level of metastatic spread in the mouse, and therefrom determining the effectiveness of the therapy.

In another aspect, methods are provided for producing tumor-reactive human cytolytic T lymphocytes, comprising: (a) implanting a specimen of a human carcinoma containing human T lymphocytes within a gonadal fat pad of an immunodeficient mouse, wherein the carcinoma is a breast, ovarian or prostate carcinoma; (b) allowing the human T lymphocytes to grow within the immunodeficient mouse; (c) isolating a human cytolytic T lymphocyte from the specimen-bearing immunodeficient mouse; and (d) evaluating the lymphocyte for the ability to kill carcinoma cells, and therefrom identifying a tumor-reactive lymphocyte.

In a related aspect, methods are provided for generating an anti-tumor antiserum, comprising: (a) implanting a specimen of a human carcinoma containing human B cells within a gonadal fat pad of an immunodeficient mouse, wherein the carcinoma is a breast, ovarian or prostate carcinoma; (b) allowing the human B cells to grow and produce human anti-tumor antibodies within the immunodeficient mouse; (c) isolating an antiserum from the immunodeficient mouse; and (d) evaluating the antiserum for the ability to bind to carcinoma cells, and therefrom identifying an anti-tumor antiserum.

In yet another related aspect, methods are provided for generating an anti-tumor monoclonal antibody, comprising: (a) implanting a specimen of a human carcinoma containing human B cells within a gonadal fat pad of an immunodeficient mouse, wherein the carcinoma is a breast, ovarian or prostate carcinoma; (b) allowing the human B cells to grow and produce human anti-tumor antibodies within the immunodeficient mouse; (c) generating a monoclonal antibody from the isolated B cells; and (d) evaluating the monoclonal antibody for the ability to bind to carcinoma cells, and therefrom identifying an anti-tumor monoclonal antibody.

Within other related aspects, the present invention provides tumor-reactive human cytolytic T lymphocytes, anti-tumor antisera, and monoclonal antibodies produced by the methods described above.

In yet another aspect, the present invention provides methods for treating cancer in a patient, wherein the cancer is a breast, ovarian or prostate cancer. In one embodiment, the method comprises administering to a patient a tumor-reactive cytolytic T lymphocyte as described above. In another embodiment, the method comprises administering to a patient an anti-tumor monoclonal antibody as described above.

These and other aspects of the present invention will become apparent upon reference to the following detailed description. All references disclosed herein are hereby incorporated by reference in their entirety as if each was incorporated individually.

DETAILED DESCRIPTION OF THE INVENTION

As noted above, the present invention is generally directed to the generation of new animal models for human carcinomas. More specifically, the animal models described herein are prepared by implantation of primary malignant human breast, ovarian or prostate tissue into a gonadal fat pad of an immunodeficient mouse. Such models may be used, for example, to grow human breast, ovarian or prostate tumors or to screen for effective therapies for such cancers. The models described herein may also be used to identify new antigens associated with human carcinomas.

Any immunodeficient mouse may be used to generate the animal models described herein. "Immunodeficient," in the context of the subject invention refers to a genetic alteration that impairs the animal's ability to mount an effective immune response. In this regard, an "effective immune response" is one which is capable of destroying invading pathogens such as (but not limited to) viruses, bacteria, parasites, malignant cells, and/or a xenogeneic or allogeneic transplant. In one preferred embodiment, the immunodeficient mouse is a severe immunodeficient (SCID) mouse, which lacks recombinase activity that is necessary for the generation of immunoglobulin and functional T cell antigen receptors, and thus does not produce functional B and T lymphocytes. Bosma and Carrol, *Ann. Rev. Immunol.* 9:323–350 (1991). In another preferred embodiment, the immunodeficient mouse is a nude mouse, which contains a genetic defect that results in the absence of a functional thymus, leading to T-cell and B-cell deficiencies. However, mice containing other immunodeficiencies (such as rag-1 or rag-2 knockouts, as described in Chen et al., *Curr. Opin. Immunol.* 6:313–319 (1994) and Guidas et al., *J. Exp. Med.* 181:1187–1195 (1995), or beige-nude mice, which also lack natural killer cells, as described in Kollmann et al., *J. Exp. Med.* 177:821–832 (1993)) may also be employed.

Carcinomas suitable for implantation are any surgical specimens of patients' primary breast, ovarian or prostate carcinomas. Patients having such carcinomas can be readily identified by those of ordinary skill in the art. In general, the implanted specimen should be a fresh biopsy specimen, trimmed of excess fat and connective tissue, and should be free of obvious necrosis or sepsis. Preferably, the specimen is minced just prior to implantation to a size no smaller than 1–2 mm. Specimens should also handled aseptically prior to implantation.

To achieve consistent tumor growth and metastasis as described herein, implantation must be within the gonadal fat pad of the immunodeficient mouse. The two halves of the gonadal fat pad occupy a large superficial region of the abdominal cavity of both male and female mice. Implantation within the gonadal fat pad may generally be achieved by drawing a portion of the gonadal fat pad out onto the external abdominal wall through a lower quadrant abdominal incision, wrapping the gonadal fat pad of the mouse around the tumor specimen, and returning the gonadal fat pad with the tumor to the abdomen. In the case of breast tumor specimens, estrogen is preferably given to the mouse at the time of implantation and every 60 days thereafter by, for example, subcutaneous insertion of a slow release estrogen pellet (1.7 mg for a cB17 scid mouse of 21–22 grams in weight). For implantation of prostate tumors, the administration of testosterone to the mouse at the time of implantation may be similarly beneficial. Tumor growth is generally observed within 5–7 weeks by visual inspection or palpitation, and tumors typically range in size from about 1 to 3 centimeters by three months after implantation. Metastatic spread to other organs may also be observed, using methods well known to those of ordinary skill in the art such as dissection and histological examination. Following growth, tumors may be passaged (i.e., portions may be removed and implanted, using the above procedure, in the gonadal fat pad of a second immunodeficient mouse).

Accordingly, in one aspect of this invention, an immunodeficient mouse having a human carcinoma specimen implanted in the gonadal fat pad is provided. Such a mouse may be used for a variety of purposes that will be apparent to those of ordinary skill in the art. For example, the mouse model may be used to grow human primary breast, ovarian or prostate carcinomas, permitting the isolation of larger quantities of human breast, ovarian or prostate cancer cells. In this aspect, implantation is performed as described above and tumor cells are harvested after sufficient growth has been achieved (generally about 2–3 months).

In another aspect of this invention, the above mouse model is used to evaluate the effectiveness of therapies for human breast, ovarian or prostate cancer. The term "therapy," as used herein, encompasses exogenous factors, such as dietary or environmental conditions, as well as pharmaceutical compositions and vaccines. In one preferred embodiment, the therapy is an immunotherapy, which may include the treatment of the tumor-bearing animal with populations of tumor-reactive immune cells. The therapy may also, or alternatively, be a gene therapy (i.e., a therapy that involves treatment of the tumor-bearing mouse with a cell population that has been manipulated to express one or more genes, the products of which may possess anti-tumor activity).

To evaluate the effectiveness of a candidate therapy, specimens of human breast, ovarian or prostate carcinomas are first implanted, preferably in a series of similar immunodeficient mice. If desired, the implanted cancer tissue may have been passaged, as described above, such that larger quantities of the tissue are available for implantation. One group of mice with implanted carcinoma tissue is then exposed to a candidate therapy, while another group (i.e., the control group) is not so exposed. Tumor growth is then evaluated in both groups of mice after an appropriate time (e.g., 2–3 months). The candidate therapy is considered effective if the size of the implanted specimen, the extent of tumor growth and/or level of metastatic spread in the mice exposed to the therapy is statistically less than the growth in the control group, and/or if the extent of tumor cell death (as evaluated through microscopic or other methods) in the mice exposed to the therapy is statistically greater than in the control group.

In still another aspect, the tumor-bearing immunodeficient mice described above may be used for the preparation of human tumor-reactive cytolytic T lymphocytes, anti-tumor antibodies and/or anti-tumor antisera. In general, the implanted specimens contain human T and B cells which are capable of growing and, in the case of B cells, producing human anti-tumor antibodies within the immunodeficient mouse. Harvesting of such human lymphocytes and/or antibodies may be performed using any appropriate technique known to those of ordinary skill in the art after sufficient growth has been achieved (generally about 1–2 months). In a preferred embodiment, human cytolytic T lymphocytes and/or antibodies may be isolated from tumor-bearing mice that have previously been repopulated with human lymphoid tissue. Such chimeric mice (e.g., SCID-hu mice) may be readily generated, and the human lymphocytes and immunoglobulin derived from such mice may be used for screening, using methods known to those of ordinary skill in the art and as described in Kaneshima et al., *Curr. Opin. Immunol.* 6:327–33 (1994).

Tumor reactive human cytolytic lymphocytes, antisera and/or B cells isolated from the tumor-bearing immunodeficient mice described above may be evaluated using a variety of methods known to those of ordinary skill in the art. For example, T cells derived from such mice may be isolated and grown in the presence of tumor cells to allow for the proliferative responses of tumor-reactive cytolytic T-cells. Tumor-reactive cytolytic lymphocytes are those lymphocytes that are capable of mediating the direct lysis of tumor cells. The ability of such tumor-reactive cytolytic T-cells to kill tumor cells can readily be measured with, for example, $^{51}$Cr release assays using methods known to those of ordinary skill in the art such as the assay described in MacDonald et al., *J. Exp. Med* 140:718 (1974). Alternatively, cytolytic T-cells may be tested for their ability to secrete cytokines using methods well known to those skilled in the art. Subsequent to such evaluation, appropriate human tumor-reactive cytolytic T-cells may be propagated in vitro, and used for purposes of either therapy or identification of tumor associated gene products recognized by such cells.

An antiserum may be evaluated for anti-tumor properties by determining whether antibodies within the antiserum are capable of binding to carcinoma cells and/or whether such antibodies recognize antigens known to be expressed by tumor cells. Similarly, isolated B cells may be used to generate monoclonal antibodies, which may be evaluated by similar means. Monoclonal antibodies may generally be prepared by, for example, using the technique of Kohler and Milstein, *Eur. J. Immunol.* 6:511–519 (1976) and improvements thereto, including immortalization of antibody-producing B-cells by infection with a transforming Herpes virus, EBV, as described in Steinitz et al., *Nature* 269:420–422 (1977); Zurauski et al., *Science* 199:1439–1441 (1979); Kozbor and Roder, *J. Immunol.* 127:1275–1280 (1981); Irie et al., *Proc. Natl. Acad. Sci. USA* 79:5666–5670 (1982); and Garzelli et al., *J. Clin. Invest.* 77:1627–1631 (1986). In either case, binding assays may be performed using any of a variety of methods known to those of ordinary skill in the art, such as those described in Harlow and Lane, *Antibodies: A Laboratory Manual,* Cold Spring Harbor Laboratory, 1988. Suitable methods include, but are not limited to, radioimmunoprecipitation, enzyme-linked immunosorbent assays and western blot assays.

Tumor-reactive cytolytic lymphocytes, antisera and antibodies (or cell lines that generate such antibodies) may be used for a variety of purposes that will be apparent to those skilled in the art such as, for example, for cancer immunotherapy. For this purpose, one or more populations of cytolytic T-cells, or one or more antibodies, may, but need not, be formulated as a pharmaceutical composition, which includes a physiologically acceptable carrier. In general, a pharmaceutical composition may be administered via any of a variety of routes, including by subcutaneous, intravenous, intraperitoneal or intradermal injection or by inhalation. While any suitable carrier known to those of ordinary skill in the art may be employed, the type of carrier will vary depending on the mode of administration. For parenteral administration, such as subcutaneous injection, the carrier preferably comprises water, saline, a fat, a wax and/or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g. polylactic galactide) may also be employed as carriers for pharmaceutical compositions. Suitable biodegradable microspheres are disclosed, for example, in U.S. Pat. Nos. 4,897,268 and 5,075,109.

An appropriate frequency of administration and dosage may generally be determined using the above animal model and subsequent clinical trials. In general, a suitable dose is a dose that, when administered as described above, is capable of generating a positive clinical result (i.e., resulting in stabilization of the cancer, or partial or complete remission). A suitable dose of cytolytic T-cells typically ranges from about $10^7$ to about $10^{10}$ cells. A suitable dose of monoclonal antibodies typically ranges from about 1–200 mg/kg body weight.

Tumor reactive cytolytic lymphocytes can also be used to identify carcinoma-associated antigens that are recognized by such cells. For example, peptides bound to the antigen binding cleft of tumor cell Class 1 MHC molecules can be separated following immunoaffinity column chromatography of carcinoma cell Class 1 MHC molecules. The resulting peptides can be further fractionated by high pressure liquid chromatography. The fractionated peptides can then be tested for their ability to trigger cytotoxic activity by tumor reactive cytolytic T-cells. The amino acid sequence of individual peptides which trigger cytolytic T-cell activity can be determined by standard tandem mass spectrometry. See, e.g., Boon et al., *Ann. Rev. Immunol.* 12:337–365 (1994). The amino acid sequence of the identified peptides can be used to generate oligonucleotide probes that may be used to isolate the genes encoding the peptides, using methods well known to those of ordinary skill in the art such as those described in Sambrook et al., *Molecular Cloning: A Laboratory Manual,* Cold Spring Harbor Laboratories, Cold Spring Harbor, N.Y. (1989) (and references cited therein). Such genes and corresponding proteins may further be used as markers for tumor diagnosis and therapy monitoring, or as anti-tumor vaccines.

Antisera, monoclonal antibodies and/or T-cells as described above may also be used for the direct expression cloning of cDNA molecules that encode tumor-associated antigens recognized by the antibodies and/or T-cells. For example, mRNA from implanted carcinomas can be transcribed into cDNA and inserted into a plasmid capable of directing the expression of the inserted cDNA(s) in mammalian cells (e.g., COS cells, CV-1 cells, African green monkey kidney cells or fibroblasts). Plasmids containing such cDNA(s) can be replicated in *E. coli* and transfected in pools into mammalian cells or into mammalian cells which have previously been transfected with human class 1 MHC genes (for presentation of such antigens to cytolytic T-cells). 24–72 hours following transfection, such mammalian cells can be used as targets for detection of expression of the products of the inserted cDNA(s). In the case of antibodies, detection can be achieved by measuring the binding of a radiolabeled antibody or by enzyme-linked immunosorbent assay. In the case of T-cells, the ability of the transfected cells to trigger cytokine release by tumor-reactive cytolytic T-cells may be detected. In either case, suitable detection methods will be readily apparent to those of ordinary skill in the art. Once a pool of cDNA(s) is identified whose products lead to detection by either tumor reactive T-cells or antibodies, such a pool can be further divided into sub pools, the sub pools may be amplified in *E. coli* and retransfected into target cells, and the detection assays may be repeated until eventually a single cDNA is isolated whose expression product is detected either by tumor reactive antibodies or by T-cells, as described above. Such cDNA molecules, as well as the corresponding full length genes and encoded proteins may further be used as markers for tumor diagnosis and therapy monitoring, or as tumor vaccines.

The following Examples are offered by way of illustration and not by way of limitation.

EXAMPLES

Example 1

Implantation of Human Carcinoma Cells in Immunodeficient Mice

This example illustrates the production of a murine model for human breast, ovarian or prostate cancer. Fresh biopsy specimens of human breast, ovarian or prostate carcinoma are received shortly after surgery. The tumors are sterily minced (in DMEM F-12 media) to a size no smaller than 1–2 mm with scissors just prior to implantation into the gonadal fat pad of SCID or nude mice. Mice are anesthetized via intraperitoneal injection of 0.25–0.3 mL of Avertin and placed on an operative metal cross. Typically, a 3 mm vertical incision is made on the right lower abdomen with scissors and the right portion of the gonadal fat pad is drawn up through the incision. One piece of tumor is placed on the surface of the gonadal fat pad and then enclosed within by wrapping the gonadal fat pad around the tumor and fixing in place with 6-0 Dexon™. The tumor/gonadal fat pad is then replaced into the abdomen. The peritoneal incision is closed with a suture. Stapler clipping is used to close the incision in the skin. At the time of implantation of a breast cancer tissue, an estrogen pellet is given subcutaneously to the back of the neck of the mice. Similarly, at the time of implantation of a prostate cancer tissue, testosterone may be administered to the mice. After the operation, the mice are warmed until they awake.

Tumor growth is discerned by visually inspecting the lower abdominal region or by palpating the region 5–7 weeks following implantation. By three months following the initial implantation, tumors range in size from about 1–3 square cm.

Table I illustrates the results obtained for a series of 32 breast carcinomas implanted into SCID mice as described above. In each case, 2–10 specimens of the primary tumor were implanted into individual mice, and the number of implanted specimens for which growth was observed, along with the total number of implanted specimens, is provided.

TABLE I

Pathological Diagnosis and Tumor Growth in SCID Mice

| Tumor # | Pathological Diagnoses | Nodal Involvement | Estrogen Receptor | Growth in SCID mice[a] |
|---|---|---|---|---|
| 7326 | Invasive Lobular Ca | − | + | 3/4 |
| 7356[b] | Invasive Ductal Ca (IDC) | + | + | 2/4 |
| 7418[b] | IDC | − | − | 1/2 |
| 7421 | Intraductal Ca (with microinvasion) | − | − | 1/2 |
| 7443[b,c,d] | IDC | + | − | 4/4 |
| 7486[c,e] | IDC | − | − | 5/5 |
| 7526 | IDC | − | + | 2/5 |
| 7528 | IDC | − | + | 3/4 |
| 7543 | IDC | − | + | 3/5 |
| 7553 | IDC | − | + | 2/4 |
| 7556[b] | Papillary Cystic Cancer | | + | 3/5 |
| 7573 | IDC | − | + | 5/8 |
| 7582 | Infiltrating Lobular Ca | + | + | 4/5 |
| 7595 | IDC | + | − | 3/3 |
| 7608[b] | IDC | − | + | 2/2 |
| 7615 | IDC | − | + | 4/5 |
| 7628[c] | IDC | + | − | 5/5 |
| 7655[f] | IDC | | | 3/3 |
| 7661 | IDC | + | + | 6/8 |
| 7679 | IDC | + | − | 5/9 |
| 7717[c] | | | | 1/3 |
| 7722[c,e] | IDC | N.A. | − | 7/7 |
| 7744 | Intraductal CA (with microinvasion) | − | − | 8/10 |
| 7748 | Infiltrating Lobular Ca | + | + | 4/10 |
| 7764[c] | IDC | + | − | 10/10 |
| 7869 | | | | 7/8 |
| 7914[c] | IDC | + | + | 4/5 |
| 7929[c] | IDC | − | − | 3/5 |
| 8099[c] | | | | 5/5 |
| 8029 | | | | 2/5 |
| 8038 | | | | 4/5 |
| 8070 | | | | 1/2 |

[a]Numbers refer to the animals in which palpable growth was obtained in the first passage out of the total number implanted with pieces of the original surgical biopsy material.
[b]Tumors that expressed Type II keratin and were demonstrated to be human by in sity hybridization using a human DNA specific probe.
[c]Showed evidence of exceptionally fast growth.
[d]Also grew in nude mice (#7356, #7418 and #7628 did not grow in nude mice).
[e]Showed evidence of metastasis to other organs in later passages.
[f]During 2nd passage, grew out as a lymphoma.

These results indicate that the above implantation method is highly effective in producing growth of primary human breast carcinoma tissue in immunodeficient mice.

Example 2

Evaluation of Pharmaceutical Agents for Anti-Tumor Activity

Following growth of the initial surgical sample to an area of greater than 3 square cm, as described in Example 1, the animal is sacrificed and the tumor tissue excised. Isolated tumor tissue is then dissected into multiple 1–2 mm pieces and such pieces are then implanted into the gonadal fat pads of multiple immunodeficient mice as detailed in Example 1. The tumor tissue may be further serially transplanted if desired, by allowing the implanted tissue to grow, excising and dissecting the tissue as described above and implanting the pieces into further immunodeficient mice.

Following tumor development in animals receiving primary surgical specimens or serially transplanted tumor tissue, tumor-bearing recipient animals are divided in multiple cohorts and subjected to treatment with a pharmaceutical agent, or combination of pharmaceutical agents suspected of having anti-tumor activity. Such treatments can be administered via multiple routes including by subcutaneous, intravenous, intraperitoneal, or intradermal injection, by aerosol inhalation or by mouth. Following a course of therapy, efficacy can be assessed by determination of relative survival, and tumor growth rates in cohorts of tumor-bearing mice who receive therapy vs. tumor-bearing mice that receive either no treatment or treatment with a placebo.

Example 3

Evaluation of Efficacy of Adoptively Transferred Immune Cell Populations for Anti-Tumor Activity Following growth of the initial surgical sample to an area of greater than 3 square cm, as described in Example 1, the animal is sacrificed and the tumor tissue excised. Isolated tumor tissue is then dissected into multiple 1–2 mm pieces and such pieces are then implanted into the gonadal fat pads of multiple immunodeficient mice as detailed in Example 1. The tumor tissue may be further serially transplanted if desired, by allowing the implanted tissue to grow, excising and dissecting the tissue as described above and implanting the pieces into further immunodeficient mice.

Following tumor development in animals receiving primary surgical specimens or serially transplanted tumor tissue, tumor-bearing recipient animals are divided in multiple cohorts and subjected to treatment with populations of immune lymphocytes suspected of having anti-tumor reactivity, or combinations of such cell populations, or combinations of such cell populations with pharmaceutical agents suspected of having anti-tumor activity. Such cells can include cytolytic T-cells, helper T-cells, dendritic cells, B-cells, lymphokine activated killer (LAK) cells or similar cells previously exposed to cytokines. Such cells can either be present as bulk populations, cell lines or clones suspected of possessing antitumor immune reactivity. Such cells can also be further manipulated by transfer of genetic information into such cells prior to their use in therapy experimentation. Treatments can be administered via multiple routes including by subcutaneous, intravenous, intraperitoneal, or intradermal injection. Following a course of therapy, efficacy can be assessed by determination of relative survival and tumor growth rates in cohorts of tumor-bearing mice that receive cellular therapy vs. tumor-bearing mice that receive either no treatment or treatment with a placebo.

Example 4

Evaluation of Efficacy of Gene Therapies for Treatment of Cancer

Following growth of the initial surgical sample to an area of greater than 3 square cm, as described in Example 1, the animal is sacrificed and the tumor tissue excised. Isolated tumor tissue is then dissected into multiple 1–2 mm pieces and such pieces are then implanted into the gonadal fat pads of multiple immunodeficient mice as detailed in Example 1. The tumor tissue may be further serially transplanted if desired, by allowing the implanted tissue to grow, excising and dissecting the tissue as described above and implanting the pieces into further immunodeficient mice.

Following tumor development in animals receiving primary surgical specimens or serially transplanted tumor tissue, tumor-bearing recipient animals are divided in multiple cohorts and subjected to treatment with a population of cells that have been manipulated so as to express a variety of genes, the products of which might possess anti-tumor activity. Such cells can either be present as bulk populations or as cell lines, and may include cells of fibroblastoid, hematopoietic, hepatic, skin, or lymphoid origin. Alternatively plasmids, or naked DNA(s) or DNA(s) encapsulated in liposomes, wherein such DNA(s) encode proteins suspected of having anti-tumor activity could be used as treatments in this model system. Treatments can be administered via multiple routes including by subcutaneous, intravenous, intraperitoneal, or intradermal injection. Following a course of therapy, efficacy can be assessed by determination of relative survival, and tumor growth rates in cohorts of tumor-bearing mice who receive gene therapy vs. tumor-bearing mice that receive either no treatment or treatment with a placebo.

Example 5

Evaluation of Effects of Different Diets on Tumor Growth

Following growth of the initial surgical sample to an area of greater than 3 square cm, as described in Example 1, the animal is sacrificed and the tumor tissue excised. Isolated tumor tissue is then dissected into multiple 1–2 mm pieces and such pieces are then implanted into the gonadal fat pads of multiple immunodeficient mice as detailed in Example 1. The tumor tissue may be further serially transplanted if desired, by allowing the implanted tissue to grow, excising and dissecting the tissue as described above and implanting the pieces into further immunodeficient mice.

Following tumor development in animals receiving primary surgical specimens or serially transplanted tumor tissue, tumor-bearing recipient animals are divided in multiple cohorts and subjected to specific diets, in order to determine the effects of such dietary changes on subsequent tumor growth and development. Diets can be altered in terms of composition and concentration of simple and complex carbohydrates, fats and proteins. Following a course of therapy, efficacy can be assessed by determination of relative survival, and tumor growth rates in cohorts of tumor-bearing mice who receive dietary therapy vs. tumor-bearing mice that receive either no treatment or treatment with a placebo.

Example 6

Evaluation of Efficacy of Cancer Vaccines

Following growth of the initial surgical sample to an area of greater than 3 square cm, as described in Example 1, the animal is sacrificed and the tumor tissue excised. Isolated tumor tissue is then dissected into multiple 1–2 mm pieces and such pieces are then implanted into the gonadal fat pads of multiple immunodeficient mice as detailed in Example 1. The tumor tissue may be further serially transplanted if desired, by allowing the implanted tissue to grow, excising and dissecting the tissue as described above and implanting the pieces into further immunodeficient mice.

Prior to or following tumor development in animals receiving primary surgical specimens or serially transplanted tumor tissue, tumor-bearing recipient animals can be repopulated with human lymphoid tissue, creating what is known to those skilled in the art as SCID-hu mice. Such animals represent essentially a chimeric animal in which the host animal is of murine origin but the animal's T and B lymphocytes are of human origin. Such animals are of utility therefore in studying human immune responses without the need for exposing patients to agents suspected of provoking an immune response. Tumor-bearing SCID-hu mice are divided in multiple cohorts and subjected to vaccination with one or more proteins or peptides suspected of evoking an anti-tumor immune response, or with one or more DNA molecules (either naked or in a vector) encoding such proteins or peptides. Such proteins, peptides or DNA molecules can be presented in a variety of aqueous or non-aqueous formulations or alternatively can be formulated in microcapsules or in liposomes. Vaccination can be administered via multiple routes including by subcutaneous, intravenous, intraperitoneal, or intradermal injection or via oral routes of administration. Following a course of vaccination, efficacy can be assessed by determination of relative survival, and tumor growth rates in cohorts of tumor-bearing mice who receive vaccine therapy vs. tumor-bearing mice that receive either no treatment or treatment with a placebo. Human anti-tumor immune responses, elicited as a result of such vaccination can also be assessed in this model.

From the foregoing, it will be appreciated that, although specific embodiments of the invention have been described herein for the purpose of illustration, various modifications may be made without deviating from the spirit and scope of the invention.

I claim:

1. An immunodeficient mouse containing human primary prostate carcinoma tissue, wherein the carcinoma tissue is implanted within a gonadal fat pad of the immunodeficient mouse and wherein the immunodeficient mouse lacks functional T cells.

2. An immunodeficient mouse containing human primary ovarian carcinoma tissue, wherein the carcinoma tissue is implanted within a gonadal fat pad of the immunodeficient mouse and wherein the immunodeficient mouse lacks functional T cells.

3. The immunodeficient mouse of any one of claims 1 or 2 wherein the mouse is a nude mouse.

4. The immunodeficient mouse of any one of claims 1 or 2 wherein the mouse is a SCID mouse.

5. A method for growing primary human prostate carcinoma tissue, comprising:
   (a) implanting a specimen of a primary human prostate carcinoma within a gonadal fat pad of an immunodeficient mouse, wherein the mouse lacks functional T cells; and
   (b) allowing the carcinoma to grow within the immunodeficient mouse.

6. A method for growing primary human ovarian carcinoma tissue, comprising:
   (a) implanting a specimen of a primary human ovarian carcinoma within a gonadal fat pad of an immunodeficient mouse, wherein the mouse lacks functional T cells; and
   (b) allowing the carcinoma to grow within the immunodeficient mouse.

7. The method of any one of claims 5 or 6 wherein the mouse is a nude mouse.

8. The method of any one of claims 5 or 6 wherein the mouse is a SCID mouse.

9. A method for evaluating the effectiveness of a potential prostate cancer therapy, comprising:
   (a) implanting a specimen of a primary or metastatic human prostate carcinoma within a gonadal fat pad of an immunodeficient mouse, wherein the mouse lacks functional T cells;
   (b) exposing the immunodeficient mouse to a candidate therapy; and
   (c) determining a change in size of the implanted specimen, the extent of tumor cell death and/or the level of metastatic spread in the mouse, and therefrom determining the effectiveness of the candidate therapy.

10. A method for evaluating the effectiveness of an potential ovarian cancer therapy, comprising:
    (a) implanting a specimen of a primary human ovarian carcinoma within a gonadal fat pad of an immunodeficient mouse, wherein the mouse lacks functional T cells;
    (b) exposing the immunodeficient mouse to a candidate therapy; and
    (c) determining a change in size of the implanted specimen, the extent of tumor cell death and/or the level of metastatic spread in the mouse, and therefrom determining the effectiveness of the candidate therapy.

11. The method of any one of claims 9 or 10 wherein the mouse is a nude mouse.

12. The method of any one of claims 9 or 10 wherein the mouse is a SCID mouse.

13. The method of any one of claims 9 or 10 wherein the therapy is an immunotherapy.

14. The method of any one of claims 9 or 10 wherein the therapy is a gene therapy.

15. The method of any one of claims 9 or 10 wherein the therapy is a dietary therapy.

* * * * *